United States Patent [19]

Springmann

[11] 3,992,443

[45] Nov. 16, 1976

[54] PROCESS FOR THE CARBOXYMETHYLATION OF ALCOHOLS OR ETHER ALCOHOLS

[75] Inventor: Hermann Springmann, Lavesum, Germany

[73] Assignee: Chemische Werke Huels Aktiengesellschaft

[22] Filed: Apr. 15, 1975

[21] Appl. No.: 568,206

[30] Foreign Application Priority Data
Apr. 17, 1974 Germany............................ 2418444

[52] U.S. Cl. .......................... 260/535 R; 260/520 R; 260/5 MK

[51] Int. Cl.$^2$........................................ C07C 59/22
[58] Field of Search .................................. 260/535 R

[56] References Cited
UNITED STATES PATENTS
2,745,857  5/1958  Batton et al. ..................... 260/535

Primary Examiner—Paul J. Killos
Attorney, Agent, or Firm—Millen, Raptes & White

[57] ABSTRACT

Alcohols, preferably ethoxylated alcohols, are carboxymethylated by reacting a mixture thereof and a salt of chloroacetic acid with an alkali hydroxide.

13 Claims, No Drawings

PROCESS FOR THE CARBOXYMETHYLATION OF ALCOHOLS OR ETHER ALCOHOLS

BACKGROUND OF THE INVENTION

This invention relates to a process for the production of carboxymethylated alcohols and alcohol ethers.

The method generally employed for the preparation of carboxymathylated ether alcohols and carboxymethylated alcohols is the reaction of alkali metal alcoholates with haloacetic acid according to the following equation:

$$RONa + ClCH_2-COONa \rightarrow ROCH_2COONa + NaCl$$

According to the state of the art, alcoholate required for this reaction are first produced from the corresponding alcohols in a separate reaction stage. In general, the production of the alcoholates is accomplished by reacting the alcohols with an alkali hydroxide (German Patent 975,850). However, when longerchain alcohols are used, the yield of the desired product during the subsequent carboxymethylation is greatly reduced. Therefore, it has frequently been necessary to react the alcohols with metallic sodium in order to obtain satisfactory yields during the carboxymethylation stage. See, for example, U.S. Pat. No. 2,183,853; British Patents 1,027,481 and 1,337,401. The use of metallic sodium, however, is expensive, complicated, and timeconsuming, and does not always lead to satisfactory results.

Accordingly, it is an object of this invention to provide a process for the production of carboxymethylated ether alcohols and carboxymethylated alcohols in a single stage. It is another object to provide a process wherein in brief reaction times, high-quality products are obtained with high degrees of conversion, even in those cases where, according to the prior art, no degree of conversion or only poor degrees of conversion can be attained. Other objects will be apparent to those skilled in the art to which this invention pertains.

SUMMARY OF THE INVENTION

According to this invention, an alcohol or an ether alcohol are carboxymethylated by reaction of a mixture thereof and a salt of chloroacetic acid with an alkali hydroxide.

DETAILED DISCUSSION

The chemical nature of the starting alcohol is not critical, so long as its hydroxy group thereof is sufficiently alcoholic in nature to form a sodium salt with sodium under conventional anhydrous conditions and it contains no other groups in the molecule reactive toward the alkali hydroxide and/or the salt of chloroacetic acid employed in the carboxymethylation reaction. Preferred starting alcohols are those wherein, excepting ether group or groups, the alcoholic hydroxy group is the sole functional group in the molecule, viz., hydrocarbon alcohols and hydrocarbon alcohol ethers.

A preferred class of starting compounds are ether alcohols, i.e, alcohols having a carbon chain interrupted by one or more ether groups. Mixtures of such compounds are especially preferred because such mixtures are readily produced by the alkoxylation, preferably ethoxylation, of one or more alcohols of the formula R-OH, wherein R has the values given below, with an alkylene oxide, e.g., of 2–4 carbon atoms, e.g., trimethylene oxide, propylene oxide and preferably ethylene oxide, to produce a mixture of hydroxyalkyl ethers thereof containing one or more oxyalkylene groups between R and the terminal hydroxy group. A wide variety of such compounds are known in the art.

Examples of suitable starting ether alcohols are those of the general formula $R-(OCH_2CH_2)_nOH$, including mixtures thereof obtainable by reacting alcohols with ethylene oxide, wherein R is aliphatic hydrocarbon, e.g., saturated or unsaturated, straight-chain or branched alkyl, or cycloalkyl of 4–20 carbon atoms or hydrocarbon aralkyl of 7–18 carbon atoms, and n is an integer from 1 to 30, preferably 2 to 7.

Examples of ether alcohols of the above formula wherein R is saturated alkyl are those wherein R is hexyl-, 2-ethylbutyl-, 2-ethylhexyl-, heptyl-, trimethylpentyl-, decyl-, dodecyl-, methyldodecyl-, tetradecyl-, pentadecyl-, hexadecyl-, octadecyl.

Examples of ether alcohols wherein R is unsaturated alkyl are those wherein R is 2-ethyl-2-hexenyl, 10-undecenyl-, oleyl Examples of ether alcohols wherein R is aralkyl are those wherein R is p-tert.-butylphenyl, p-octylphenyl, o-methylphenyl, p-nonylphenyl, p-dodecylphenyl.

Specific examples of starting alcohol ethers, in the case of a single starting alcohol, are each of the above illustrations of values for R in compounds of the formula $R-(OCH_2CH_2)_n-OH$ wherein n is the integer 1, 2, 4, 7, 25, etc. In the case of the preferred starting mixtures of such ether alcohols, n is the average of the values for n for each compound of the mixture and thus can be a whole number or fraction, e.g., 4.1, 4.5, 6.5, etc.

Examples of suitable starting alcohols are saturated or unsaturated, straight-chain or branched, aliphatic or araliphatic alcohols of 4–20 carbon atoms, or alkylated phenols of up to 18 carbon atoms.

Examples of starting aliphatic alcohols on which the alcohol group is the sole functional group are those of the formula R-OH wherein R is butyl, pentyl, hexyl, methylbutyl, ethylbutyl, heptyl, octyl, ethylhexyl, nonyl, trimethylhexyl, decyl, dodecyl, tridecyl, tetradecyl, entadecyl, hexadecyl, octadecyl, eicosyl.

Examples of starting araliphatic alcohols are those in which the alcohol group is the sole functional group are those of the formula R-OH wherein R is phenylethyl, phenylpropyl, phenylbutyl, methylphenylethyl.

Examples of starting alkylated phenols in which the phenolic hydroxy group is the sole functional group are those of the formula R-OH wherein R is p-tert.-butylphenyl, o-octylphenyl, o-methylphenyl, p-nonylphenyl, p-dodecylphenyl.

Especially suitable starting alcohol ethers are reaction products of ethylene oxide with alcohols as produced during the oxo reaction, and reaction products of lauryl and tetradecyl alcohols with 4.5 moles of ethylene oxide, i.e., a mixture of compounds of the above formula wherein R is lauryl or tetradecyl and n has an average value of 4.5.

In general, equimolar mixtures of startingalcohol and chloroacetate salt are employed. However, this ratio can be varied, if desired. When producing carboxymethylates to be utilized as raw materials for detergents, the process is conducted, for example, frequently with molar excess of the ether alcohol, e.g., 20 to 40%, since a proportion of unreacted ether alcohol in the carboxymethylate improves the properties of the mixture with respect to laundering technology. Conversely, if it is desired to convert the alcohol or ether alcohol to a maximum extent, a molar excess, e.g., a 20–50% molar excess, of chloroacetate, based on the alcohol, easily effects a practically complete conversion of the alcohols into the carboxymethylate.

The sodium salt of chloroacetic acid is generally employed, but it is also possible to use other salts thereof, e.g., the potassium or lithium salt. The chloroacetic acid salt can also be formed directly in the reaction mixture from chloroacetic acid, in which case, it is merely necessary to employ correspondingly larger quantities of alkali hydroxide.

Since the alkali hydroxide must react with the chlorine atom of the chloroacetate salt, to achieve complete reaction equimolar amounts of the hydroxide and chloroacetate salt are employed. The use of a molar excess of alkali hydroxide achieves no apparent advantage and necessitates its removal from the reaction product.

Suitable alkali hydroxides are lithium, sodium, and potassium hydroxide. In general, however, sodium hydroxide is used for economical reasons.

A special advantage of the process is that it is possible to utilize aqueous alkali hydroxide solutions as well as solid alkali hydroxides without the reaction being impaired. For this purpose, the addition of a 40–70% by weight solution of alkali hydroxide proved to be suitable. Below an alkali hydroxide concentration of 40% by weight, the excessive water concentration strongly promotes the hydrolysis of the chloroacetate to the glycolate, thus making the reaction commercially unsuitable, and above 70% by weight, the physical characteristic of the alkali hydroxide solution approaches increasingly that of anhydrous alkali hydroxide. In other words, the solution is solid even at elevated temperatures, so that there is no longer an advantage to be derived from the viewpoints of process technology by the use of such a solution. When using aqueous alkali hydroxide solution, it can be expedient to keep the reactor at reduced pressure during the addition of the alkali hydroxide solution, insofar as the boiling point of the starting alcohol permits such a procedure. Thereby, the water introduced into the reaction system can be removed substantially to the same extent to which it is fed into the reaction vessel. In this way, high yields can be attained even when using a dilute aqueous alkali hydroxide solution without the necessity of introducing an excess of chloroacetate.

The reaction is ordinarily conducted at ambient or slightly elevated temperatures, e.g., 20° to 60° C. Below 20° C., the reaction takes place too slowly for a commercial process and above 60° C., the formation of by-products occurs to an increasing extent. A reaction temperature of 25°–40° C. is especially suitable. This temperature is also particularly advantageous when using aqueous alkali hydroxide solution, to maximally suppress the hydrolysis of the chloroacetate to the glycolic acid salt, which takes place as a secondary reaction.

The reaction products are worked up in a conventional manner by acidifying with a dilute acid, such as sulfuric or hydrochloric acid. During gentle heating, the aqueous phase containing the alkali salts, e.g., sodium chloride and sodium glycolate, is separated from the organic phase. In case of alcohols having a carbon atom number smaller than 10, this phase separation does not take place. In such cases, the reaction products can be separated by extraction with ether, or they can be made into a slurry with a low-boiling solvent such as methanol, which does not dissolve NaCl or other alkali salts, and the solvent solution can then be filtered off from the NaCl or other salt after heating to 50°–60° C. The solvent used in this step can thereafter be removed from the product by distillation.

A particular advantage of the process is that it also very easily carboxymethylates alcohols which, as is known, do not lend themselves as readily to carboxymethylation as their reaction products with ethylene oxide. Whereas lauryl alcohol, under the conditions of Comparative Example 1, is converted practically not at all to the corresponding ether acid, even with the use of metallic sodium in place of solid sodium hydroxide, so that a yield of only 42%, based on the lauryl alcohol, is obtained (Comparative Example 2), the process of this invention, in contrast to the above, surprisingly provides a yield of 65% (Example 2).

Additional advantages are that the process of this invention can be conducted more simply, as well as more rapidly and more economically because of the elimination of the stage of alcoholate formation. Furthermore, the possibility of using aqueous alkali hydroxide solutions is a considerable advance in the art.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

A commercially available mixture consisting of 50% by weight of lauryl alcohol and 50% by weight of tetradecyl alcohol (trade name "Alfol" 1214) is reacted in the usual manner with 4.5 moles of ethylene oxide. The thus-formed oxyethylate showed the following composition:

|  |  | Ethylene Oxide Distribution | | |
|---|---|---|---|---|
| ethylene oxide (EO)content: | 49.5% | (calculated free of polydiol) | | |
| Free polydiol | 0.5% | Fatty alcohol + | 0 | EO: 9.2% |
| Water | 0.04% |  | 1 | ": 6.0% |
|  |  |  | 2 | ": 7.8% |
| Sodium | 0.04% |  | 3 | ": 8.3% |
|  |  |  | 4 | ": 8.7% |
| OH-Number | 144.9 |  | 5 | ": 8.3% |
|  |  |  | 6 | ": 8.3% |
| Alkali number | 0.56 |  | 7 | ": 7.9% |
|  |  |  | 8 | ": 7.5% |
| Average |  |  | 9 | ": 6.5% |
| molecular weight | ~390 |  | 10 | ": 5.5% |

-continued

| Ethylene Oxide Distribution | |
|---|---|
| 11 ″: | 4.6% |
| 12 ″: | 3.5% |
| 13 ″: | 2.7% |
| 14 ″: | 1.8% |
| 15 ″: | 1.3% |
| 16 ″: | 0.8% |
| 17 ″: | 0.6% |
| 18 ″: | 0.3% |
| 19 ″: | 0.2% |
| 20 ″: | 0.1% |
| Average degree of (EO)ethoxylation | : 4.4 mole EO |

780 g. of the oxyethylate (~2 moles) is mixed under thorough agitation with 247 g. of sodium chloroacetate (94.2% strength, ~2 moles) during a period of 25 minutes at 25° C. Then, 82 g. (98% strength) pulverized sodium hydroxide (~2 moles) is uniformly introduced in incremental portions at this temperature within 4 hours. After the addition of the sodium hydroxide, the reaction mixture is stirred for another 7 hours at a temperature of 40° C.

The reaction product is then combined with 930 ml. of 10% sulfuric acid, well intermixed, and heated to 90° C. The mixture is allowed to stand for a short period of time, during which it separates into an upper, organic phase (949 g.) and a lower, aqueous phase. The organic phase has an acid number of 97.5: from this, a content of free polyether acid is calculated of 79.3% in the upper phase. A determination of the acid by two-phase titration (in water/chloroform with "Safranin T" as the indicator) yields, with satisfactory coincidence, a content of 81.0% by weight of polyether acid. Considering the water content of 8.8% in the organic phase, a content of 88.8% by weight of polyether acid is found, based on the anhydrous substance.

The yield of polyether acid is 85.8% of theory, based on the oxyethylate employed.

COMPARATIVE EXAMPLE FOR EXAMPLE 1

Under agitation, 120 g. (3 moles) of solid pulverized sodium hydroxide is gradually introduced within 2 hours at 40° C. into 1,170 g. of the same oxyethylate (3 moles) as used in Example 1. The mixture is stirred for about 2 hours at this temperature; during the course of one-half hour, the temperature is raised to 60° C. and the stirring is continued at this temperature for another 2 hours. Thereafter, 349.5 g. of sodium chloroacetate (~3 moles) is gradually added under agitation in 5 portions (about 2 hours) at 60° C. After the last portion, the mixture is further agitated for 6½ hours at 60° C., so that a total reaction time of 13 hours results, including the time for adding the sodium chloroacetate. The reaction is conducted under a nitrogen atmosphere during the entire duration thereof.

The reaction product is then combined, in an agitator-equipped vessel, with 1,000 ml. of 10% sulfuric acid and heated under constant agitation to 85° C. The product then is allowed to stand without being agitated for about 20 minutes; the temperature is maintained at 85°–90° C. The mixture separates into two layers, the top layer, which is the organic phase (1,413 g.), containing the carboxymethylated oxyethylate in the form of the free acid, and the lower, aqueous phase (1,265 g.) containing primarily the sodium chloride formed during the reaction.

The two phases can readily be separated from each other. By means of titration (two-phase titration in water/chloroform with "Safranin T" as the indicator), 67.5% by weight of polyether acid is determined in the organic phase; the water content is 7.2% by weight. Consequently, a content of 72.8% by weight of polyether acid, based on the anhydrous substance, is calculated therefrom. The yield of polyether acid is 71.3% of theory, based on the oxyethylate employed.

EXAMPLE 2

372 g. of lauryl alcohol (2 moles) is thoroughly mixed with 246 g. of sodium chloroacetate (95% strength, 2 moles) and, at 50°–60° C., 81.7 g. of sodium hydroxide (98% strength, 2 moles) is added in 25 portions within 4 hours. The reaction mixture is combined with 200 g. of lauryl alcohol for purposes of dilution and then agitated for 4½ hours at 60° C. and for another hour at 70° C.

After the addition of 970 ml. of 10% sulfuric acid, the reaction mixture separates into two phases upon being heated to 95°–100° C. The upper, organic phase which also contains the lauryl alcohol added as a diluent is separated after 15 minutes.

In this way, 666 g. of a product is obtained having the following values: acid number 99.4; ether acid content: 50.2% by weight (calculated as the anhydrous substance); water content: 4.5% by weight. The yield of ether acid amounts to 65.7% of theory.

COMPARATIVE EXAMPLE FOR EXAMPLE 2

During a period of 15 minutes, 23 g. of sodium is introduced at 60° C. in finely divided form into 744 g. of lauryl alcohol (4 moles); the mixture is then stirred for another 7½ hours at 100°–110° C. until the metallic sodium has been completely dissolved. The mixture is then cooled off to 60° C. Within 2½ hours, 116.5 g. (1 mole) of sodium chloroacetate is added in 5 portions, and the mixture is agitated for another 6 hours. During the entire experiment, the reaction mixture was maintained under a nitrogen atmosphere.

After the addition of 3,000 ml. of petroleum ether, the mixture is stirred for 2 hours at room temperature and then suction filtered from the salt residue (344 g.). This residue is combined with 356 ml. of 10% sulfuric acid and agitated for 20 minutes at 90° C. The phases, which form after allowing the reaction mixture to stand briefly, are separated, thus obtaining 510.5 g. of an aqueous phase and 254 g. of an organic phase.

The latter contains, in addition to 28.5% by weight of water, 40.6% by weight of ether acid (= 103 g.). The yield of ether acid is 42.6% of theory.

EXAMPLE 3

408 g. of n-1-hexanol (4 moles) is mixed with 246 g. of sodium chloroacetate (95% strength, 2 moles). At a temperature of 40° C., 81.7 g. of sodium hydroxide (98% strength, 2 moles) is added in powder form under vigorous agitation to this mixture in 17 portions during the course of 4 hours.

The reaction mixture is further agitated for 17 hours at 40° C. and for 1 hour at 50° C., the mixture being maintained under a nitrogen atmosphere.

The thus-obtained product is first combined with 700 ml. of water; then, 900 ml. of ether is added and the mixture is stirred. The ether phase is then separated from the aqueous phase. The latter is extracted 5 times with respectively 400 ml. of ether. The ether phases are combined and washed with 180 ml. of water; the wash water is again extracted 3 times with ether. Finally, all ether phases are combined and distilled on a forced-circulation evaporator. A residue of 207 g. is obtained, constituting unreacted, excess n-hexanol.

The aqueous phase is combined with the wash water, set to pH 2 with concentrated hydrochloric acid, and extracted 4 times with ether. The ether phase is washed free of acid with water, dried with sodium sulfate, and the ether is then removed on a forced-circulation evaporator. A residue of 305 g. is thus obtained, having an acid number of 322 and an ester number of 21.6. This corresponds to a theoretical yield of 87.7%.

By distillation of the residue, 257 g. of a fraction is obtained which boils at 92°-97° C./0.15 - 0.2 torr [mm. Hg], with a calculated value of $n_{D4}^{20}$ of 1.4341 and a content of 94.9%, corresponding to a theoretical yield of 76.3% of pure substance.

EXAMPLE 4

585 g. of the oxyethylate (1.5 moles) used for Example 1 is thoroughly mixed under agitation with 184 g. of sodium chloroacetate (95% strength, 1.5 moles) during a period of 30 minutes at 20°-25° C. Then, at a temperature of 25°-30° C., 70% aqueous sodium hydroxide solution having a temperature of 75°-80° C. is added dropwise under thorough agitation from a heated dropping funnel within 1.5 hours.

After another agitation period of 8 hours at 25°-30° C., the reaction mixture is set to pH 2 with 10% sulfuric acid and then heated to 90°-95° C., thus obtaining an upper, organic phase (720 g.) and a lower, aqueous phase (977 g.) which are separated from each other after allowing the mixture to stand for a short period of time.

The organic phase contains, in addition to 8.7% by weight of water, 76.4% by weight of polyether acid, so that a content of 83.7% by weight of anhydrous substance is calculated therefrom.

The polyether acid yield is 81.8% of theory, based on the oxyethylate employed.

EXAMPLE 5

780 g. (2 moles) of the oxyethylate employed for Example 1 is combined with 238 g. of sodium chloroacetate (98%, 2 moles), and then 161 g. of 49.5% strength aqueous sodium hydroxide solution (2 moles) is added dropwise under agitation during a period of 4 hours, at a temperature of 40°C. and reduced pressure (0.2 torr). Simultaneously, the water is collected in a well-cooled trap. After the alkaline solution has been added dropwise, the thus-collected amount of water is 87.4 g. The mixture is stirred for another 4 hours at 40° C. and then again for 10 hours at 60° C. After this time, the quantity of water separated in total is 110.3 g., corresponding to 95% of the theoretically possible value.

The reaction mixture is set to pH 2 with 10% aqueous sulfuric acid and heated to a temperature of 95° C. The upper, organic phase (953 g.) contains, in addition to 8.1% by weight of water, 83.4% by weight of polyether acid, corresponding to a value, calculated as the anhydrous substance, of 90.7% by weight. The yield of polyether acid is 88.5% of theory, based on the oxyethylate employed.

COMPARATIVE EXAMPLE FOR EXAMPLE 5

780 g. (2 moles) of the oxyethylate used for Example 1 is combined with 160 g. of 50% aqueous sodium hydroxide solution and 40 g. of water in a heated dropping funnel at 60° C. by constant agitation. The water is withdrawn from the mixture within 4 hours under a pressure of 2.5 torr by means of distillation in a thin-film evaporator at 100° C; this water is collected in a cooling trap. By way of a capillary, a weak nitrogen stream is introduced into the entire apparatus.

Yield: 790 g. of sodium oxyethylate having a water content of 1.92% by weight. The amount of water condensed in the cooling trap is 138 g., so that, in total, 153 g. of water, i.e., 98% of the theoretically possible quantity, is obtained.

Under agitation, 220 g. of sodium chloroacetate is introduced within 2 hours in 5 portions at a temperature of 60° C. into 780 g. of the thus-obtained sodium oxyethylate (corresponding to 1.89 moles of sodium oxyethylate). Thereafter, the mixture is agitated for another 6½ hours at this temperature. The product is maintained under a nitrogen atmosphere during the entire procedure.

Subsequently, such an amount of 10% sulfuric acid is added to the reaction mixture that a pH of 2 is attained, whereupon the product is separated from the thus-formed aqueous phase by heating to 95° C. The separated upper organic phase (902 g.) contains, in addition to 7.8% by weight of water, 68.3% by weight of polyether acid, so that a value of 76.5% by weight of polyether acid is calculated, based on the dry substance. The yield of polyether acid is 72.3% of theory, based on the sodium oxyethylate employed.

EXAMPLE 6

780 g. (2 moles) of the oxyethylate used for Example 1 is thoroughly mixed with 190 g. of sodium chloroacetate (98%, 1.6 moles). Under agitation, 129 g. of 49.5% sodium hydroxide solution (1.6 moles) is added dropwise to this mixture at a temperature of 35° C. and reduced pressure (0.2 torr) within 4½ hours. At the same time, the water introduced with the alkaline solution and the water additionally formed by the reaction is condensed in a cooling trap. After the alkaline solution has been added dropwise, the mixture is stirred for another 2 hours at 40° C. under vacuum (0.2 torr) and for 16 hours under normal pressure (760 torr), as well as another 5 hours at 60° C.

The reaction mixture is then adjusted to pH 1.9 with 10% sulfuric acid and heated to 95° C. The upper, organic phase (950 g.) is separated from the lower, aqueous phase. This organic phase contains, in addition to 8.2% by weight of water, 72.4% by weight of polyether acid, corresponding to a value, calculated in the anhydrous form, of 78.9% by weight. The yield of polyether acid is 76.8% of theory, based on 780 g. of oxyethylate.

EXAMPLE 7

A commercially available mixture of 50% by weight of lauryl alcohol and 50% by weight of tetradecyl alcohol (trade name "Alfol" 1214) is reacted with 25 moles of ethylene oxide in the usual manner. The OH-number of the oxyethylate is 45.7 (MW 1,225).

780 g. of this oxyethylate (corresponding to 0.64 mole) is combined with 78 g. of sodium chloroacetate (95%, 0.64 mole) and, under agitation, 26 g. of sodium hydroxide (98%, 0.64 mole) in the form of a powder is introduced at a temperature of 50° C. in 10 portions during the course of 200 minutes. Thereafter, the mixture is further agitated for 4 hours at 50° C. to complete the reaction.

The reaction mixture is set to pH 2 with 10% sulfuric acid and heated to 110° C. To improve the phase separation, 40 ml. of ethanol is added. From the thus-separated organic phase, the ethanol is blown off with nitrogen at 95° C.

The organic phase (798 g.) contains, in addition to 0.9% by weight of water, 90.8% by weight of polyether acid, corresponding to a value, calculated as the anhydrous substance, of 91.6% by weight of polyether acid. The yield of polyether acid is 88.2% of theory, based on the reacted oxyethylate.

COMPARATIVE EXAMPLE FOR EXAMPLE 7

At a temperature of 60° C., 918 g. (0.75 mole) of the oxyethylate utilized in Example 7 is thoroughly mixed under agitation with 30 g. of pulverized sodium hydroxide (0.75 mole) during a period of 3 hours. Thereafter, 92 g. of sodium chloroacetate (0.75 mole, 95% strength) is added within 2 hours in 5 portions at 60° C. The reaction mixture is stirred at a temperature of 60° C. for another 6½ hours and constantly maintained under a nitrogen atmosphere during this process.

The reaction product is set to pH 2.0 with 10% sulfuric acid and heated to 95° C. During this step, the mixture separates into an upper, organic phase (1,072 g.) and a lower, aqueous phase (370 g.) after about 90 minutes. The organic phase (1,072 g.) contains, in addition to 13.4% by weight of water, 66.5% by weight of polyether acid, corresponding to a content of 76.9% by weight, based on the anhydrous substance. The yield of polyether acid is 73.9% of theory, based on the reacted oxyethylate.

EXAMPLE 8

1,200 g. of triethylene glycol (8 moles) is combined with 224 g. (4 moles) of pulverized potassium hydroxide and agitated for 1 hour at a temperature of 90° C. After the potassium hydroxide has been dissolved completely, 984 g. (4.8 moles) of lauryl chloride is added dropwise during the course of 2 hours. The reaction mixture is then agitated for another 12 hours at a temperature of 120°–130° C. The reaction is conducted under a nitrogen atmosphere.

After cooling to 35° C., the thus-formed potassium chloride is vacuum-filtered (272 g.), the upper layer is separated and distilled over a short column at 0.8 torr. The product passing over between 100° and 192° C. (764 g.) is once again distilled. At 0.2 torr and 158°–163° C., 657 g. of a product is obtained having the $n_D^{20}$ of 1.4510. The content of triethylene glycol mono-n-dodecyl ether, determined by gas chromatography, is 96.3% by weight.

318 g. of the ether (~ 1 mole) is combined with 123 g. of sodium chloroacetate (95% strength, 1 mole). Then, 40.8 g. of pulverized sodium hydroxide (98% strength, 1 mole) is added within 4 hours in 13 portions at a temperature of 40° C. Subsequently, the mixture is stirred for another 6 hours at 40° C.

The reaction product is set to pH 2 with 10% sulfuric acid and separated into two phases by heating to 95° C. The upper, organic phase (404 g.) is separated; this phase contains, in addition to 8.5% by weight of water, 83.1% by weight of polyether acid, corresponding to a content of 90.8% by weight, based on the anhydrous substance.

The yield of polyether acid corresponds to 89.3% of theory, based on the triethylene glycol mono-n-dodecyl ether employed.

EXAMPLE 9

242 g. of an oxyethylate, produced from oleyl alcohol and 7 moles of ethylene oxide (0.47 mole, OH-number 108.4) is combined with 57.7 g. of sodium chloroacetate (95%, 0.47 mole). At a temperature of 40° C., 19.2 g. of pulverized sodium hydroxide (98%, 0.47 mole) is added to this mixture in 10 portions during the course of 3 hours. The mixture is then stirred for another 6 hours at 40° C.

The reaction mixture is thereafter brought to pH 1.9 by adding 10% sulfuric acid and heated to about 100° C. To facilitate the phase separation, 60 ml. of ethanol can be added before the heating step. The upper, organic phase (280 g.) contains, after the lower, aqueous phase has been separated, 87.8% by weight of polyether acid in addition to 6.3% by weight of water. Based on the anhydrous substance, this results in a content of 93.7% by weight of polyether acid. The yield of polyether acid corresponds to 91.5% of theory, based on the oxyethylate employed.

COMPARATIVE EXAMPLE FOR EXAMPLE 9

80 g. of pulverized sodium hydroxide (2 moles) is added to 1,032 g. of the oxyethylate utilized in Example 9 (2 moles); the mixture is first stirred for 2 hours at 40° C. and then for another 2 hours at 60° C.

Subsequently, 233 g. of sodium chloroacetate (2 moles) is introduced in 5 portions within 2 hours at 60° C. The reaction mixture is then agitated thoroughly for another 6½ hours at 60° C. During the entire experiment, the reaction mixture is maintained under a nitrogen atmosphere.

By acidification with 10% sulfuric acid, the polyether acid (1,075 g.) is separated from the reaction product as described in Example 9. In addition to 0.29% by weight of water, a content of 67.7% by weight of polyether acid is found, corresponding to a content of 68% by weight of anhydrous reaction product.

The yield of polyether acid corresponds to 63.5% of theory, based on the oxyethylate utilized.

EXAMPLE 10

730 g. of an oxyethylate (obtained by a conventional reaction of 4.5 moles of ethylene oxide with a $C_{11}$-$C_{14}$ oxo alcohol) having an OH-number of 147.7 (~ 2 moles) is mixed with 246 g. of sodium chloroacetate (95%, 2 moles). Then, 81.7 g. of powdered sodium hydroxide (98%, 2 moles) is added in 17 portions during the course of 4 hours at a temperature of 40° C. At this temperature, the mixture is stirred for another 5½ hours.

The reaction mixture is then set to pH 2 with 10% sulfuric acid and heated to a temperature of 90° C. After 30 minutes, the upper, organic phase (881 g.) is separated from the lower, aqueous phase (1,127 g.). The organic phase contains, in addition to 8.7% by weight of water, 76.3% by weight of polyether acid, corresponding to a value of 83.7% by weight, based on the anhydrous substance.

The yield of polyether acid corresponds to 97% of theory, based on the oxyethylate employed.

EXAMPLE 11

585 g. of the oxyethylate used for Example 1 (1.5 moles) is mixed with 221 g. of sodium chloroacetate (95%, 1.8 moles) and stirred for 15 minutes at a temperature of 25°–40° C. Under constant agitation, 73.4 g. (98%, 1.8 mole) of pulverized sodium hydroxide is introduced into the mixture in 17 portions within 4 hours. During this time, a reaction temperature of 40°–44° C. is being maintained. After a further agitation period of 17 hours, the sodium hydroxide has been extensively consumed; the alkali number is 1.05.

At a product temperature of 45° C. and at 0.2 torr, the thus-formed water of reaction (26 g.) is first withdrawn. Then, another 55 g. of sodium chloroacetate (95%, 0.45 mole) is added and thereafter another 18.4 g. of sodium hydroxide (98%, 0.45 mole) is introduced during the course of one hour in finely pulverized form. After agitation overnight, the charge shows an alkali number of 14.7. The reaction temperature is elevated to 55°–60° C. and the mixture is once again agitated for 3 hours at this temperature; the alkali number decreases to 6.4. During the entire experiment, the reaction mixture is maintained under a nitrogen atmosphere.

29 g. of the reaction mixture is withdrawn for purposes of analysis.

The reaction mixture is then set to pH 2 with 10% sulfuric acid and heated to 95° C. The mixture separates into an upper, organic phase (714 g.) and a lower, aqueous phase (1,345 g.). The organic phase contains, in addition to 89.6% by weight of polyether acid, 9.1% by weight of water, calculated as a content of 98.6% by weight of anhydrous polyether acid. Taking the amount of 29 g. into account, which has been used up for analytical purposes, a yield of 99.8% of polyether acid is obtained at a degree of conversion of 98.6%, based on the oxyethylate employed.

EXAMPLE 12

176 g. of 2-methyl-1-butanol (2 moles) is heated to 50° C. and combined under agitation with 122.5 g. of sodium chloroacetate (95%, 1 mole). After 15 minutes, 40.8 g. of pulverized sodium hydroxide (98%, 1 mole) is added thereto in 12 portions within 3½ hours.

The mixture is further agitated at a temperature of 50° C. for another 18½ hours.

Then, the reaction mixture is combined with 300 ml. of water, thereby obtaining a complete solution. The aqueous solution is extracted 6 times with respectively 200 ml. of ether; the ether extracts are combined and washed once with water. The wash water, in turn, is extracted 3 times with ether. The ether phases are combined, and the ether is discharged on a forced-circulation evaporator. A residue remains of 116.4 g. of 2-methyl-1-butanol (1.3 moles).

The combined aqueous phases are set to pH 2 with concentrated hydrochloric acid and extracted 6 times with respectively 200 ml. of ether. The ether phases are combined and washed neutral with aqueous sodium bicarbonate solution, dried over sodium sulfate, and then the ether is withdrawn by means of a forced-circulation evaporator. A residue remains of 69.6 g. of ether with an acid number of 378, corresponding to an ether acid content of 98.4% by weight.

A sample of this acid is distilled over a short column (b.p. 75°–77° C. at 0.15 torr). The thus-obtained pure acid has $n_D^{20}$ of 1.4296 and an acid number of 382.5. A content of 98.9% is determined by gas chromatography. The yield is 47% of theory.

The preceding examples can be repeated with similar success by substituting the generically and specifically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the production of carboxymethylated alcohols by the reaction of an alcohol, a salt of chloroacetic acid and an alkali hydroxide, the improvement which comprises adding lithium hydroxide, potassium hydroxide or sodium hydroxide to a mixture of the alcohol and the salt of chloroacetic acid at a temperature of 20° to 65° C.

2. A process according to claim 1 wherein the alkali hydroxide is added in solid form.

3. A process according to claim 1 wherein the reaction is conducted at 25°–40° C.

4. A process according to claim 1 wherein the alkali hydroxide is added in the form of an aqueous solution containing 40–70% by weight of alkali hydroxide.

5. A process according to claim 3 wherein the reaction is conducted at an elevated temperature and reduced pressure and water is removed from the reaction mixture at a rate approximately equal to the rate at which water is added thereto.

6. A process according to claim 1 wherein an amount of alkali hydroxide chemically equivalent to the salt of chloroacetic acid is employed.

7. A process according to claim 1 wherein the alkali hydroxide is sodium hydroxide.

8. A process according to claim 1 wherein the salt of chloroacetic acid is sodium chloroacetate.

9. A process according to claim 1 wherein the starting alcohol is a compound or mixture of compounds of the formula R-(OCH$_2$CH$_2$)$_n$OH wherein R is aliphatic hydrocarbon of 4–20 carbon atoms or hydrocarbon aralkyl of 7–18 carbon atoms.

10. A process according to claim 8 wherein the starting alcohol is ethoxylated lauryl or tetradecyl alcohol or a mixture thereof.

11. A process according to claim 8 wherein a mixture of starting alcohol and sodium chloroacetate is reacted with an amount of sodium hydroxide chemically equivalent to the sodium chloroacetate.

12. A process according to claim 10 wherein the sodium hydroxide is added to the mixture in the form of an aqueous solution thereof containing 40–70% by weight of sodium hydroxide, the reaction is conducted at 25°–40° C. and at reduced pressure, and water is removed from the reaction mixture at a rate approximately equal to the rate at which water is added thereto.

13. A process according to claim 10 wherein the sodium hydroxide is added to the mixture in solid form and the reaction is conducted at 25°–40° C.

* * * * *